(12) United States Patent
HinKamp (10) Patent No.: US 7,609,155 B2
(45) Date of Patent: Oct. 27, 2009

(54) SYSTEM PROVIDING MEDICAL PERSONNEL WITH IMMEDIATE CRITICAL DATA FOR EMERGENCY TREATMENTS

(76) Inventor: Thomas J. HinKamp, 200 Woodley Dr., Winnetka, IL (US) 60093

( * ) Notice: Subject to any disclaimer, the term of this patent is extended or adjusted under 35 U.S.C. 154(b) by 276 days.

(21) Appl. No.: 11/510,317

(22) Filed: Aug. 25, 2006

(65) Prior Publication Data

US 2007/0046476 A1    Mar. 1, 2007

Related U.S. Application Data

(60) Provisional application No. 60/711,318, filed on Aug. 25, 2005.

(51) Int. Cl.
*G08B 1/08*    (2006.01)
(52) U.S. Cl. ................. 340/539.12; 340/573.1
(58) Field of Classification Search ............ 340/539.12, 340/573.1, 572.1, 572.7, 572.8; 600/300; 705/2
See application file for complete search history.

(56) References Cited

U.S. PATENT DOCUMENTS

| | | | |
|---|---|---|---|
| 5,012,229 A | | 4/1991 | Lennon et al. |
| 5,337,290 A | | 8/1994 | Ventiniglia et al. |
| 5,649,381 A | | 7/1997 | Studer |
| 5,877,742 A | | 3/1999 | Klink |
| 5,883,576 A | | 3/1999 | De La Huerga |
| 5,986,562 A | * | 11/1999 | Nikolich ................. 340/573.1 |
| 6,375,612 B1 | * | 4/2002 | Guichon et al. ............. 600/300 |
| 6,419,158 B2 | | 7/2002 | Hooglander |
| 6,724,690 B1 | | 4/2004 | Endo et al. |
| 6,747,561 B1 | * | 6/2004 | Reeves ..................... 340/573.1 |

(Continued)

FOREIGN PATENT DOCUMENTS

WO    WO 03083905 A2    10/2003

OTHER PUBLICATIONS

Bailes, et al., Abstract entitled "NMR Imaging Of The Brain Using Spin Echo Sequences," Clinical Radiology, 1982, 33 (4), pp. 395-414.

(Continued)

*Primary Examiner*—John A Tweel, Jr.
(74) *Attorney, Agent, or Firm*—Leydig, Voit & Mayer, Ltd.

(57) ABSTRACT

An RFID transponder on a person or animal provides the health care or security personnel with the critical information when the personnel employs a reader terminal capable of reading the RFID transponder. The transponder, after being interrogated by the reader, supplies the critical data such as name, blood type, allergies, directives, medicines, and emergency contact numbers. The reader immediately displays such critical information on its screen. The RFID tag can substantiate that it belongs to its owner. This identification process can involve biometric analysis. The reader terminal downloads additional data from a server and the additional data is presented on a reader terminal's screen. The server queries the wireless carrier for reader terminal's location data, correlates the reader location data with hospital location data, and sends the critical information to the nearby hospitals. Additionally, the server sends alert information to other firms or individuals contained in the transponder wearer's data record. The RFID tag is the healthcare record. It relates and integrates into a larger database and network. It proves its owner and through wireless technology identifies location and other data characteristics of its owner.

42 Claims, 7 Drawing Sheets

U.S. PATENT DOCUMENTS

| | | | |
|---|---|---|---|
| 6,845,063 | B2 | 1/2005 | Mitchell |
| 7,161,484 | B2* | 1/2007 | Tsoukalis .............. 340/539.12 |
| 7,333,013 | B2* | 2/2008 | Berger ................... 340/539.12 |
| 2003/0174049 | A1* | 9/2003 | Beigel et al. ............. 340/10.42 |
| 2005/0173509 | A1 | 8/2005 | Miettinen |
| 2007/0109117 | A1* | 5/2007 | Heitzmann et al. ...... 340/539.12 |
| 2008/0088436 | A1* | 4/2008 | Reeves et al. .......... 340/539.12 |
| 2008/0129486 | A1* | 6/2008 | Jeckelmann et al. ... 340/539.12 |
| 2008/0191866 | A1* | 8/2008 | Falck et al. ............ 340/539.12 |

OTHER PUBLICATIONS

Benjamin, Abstract entitled "Making Paper Smarter: When Paper Starts To think," Distribution Sales and Management, Jun. 2003, vol. 44, No. 5.

Cain et al., Abstract entitled "Energy Harvesting For DNA Gene Sifting And Sorting," International Journal of Parallel and Distributed Systems & Networks, 2001, vol. 4, No. 3, pp. 140-149, Acta Press, USA.

Cascetta et al., Abstract entitled "Automatic Systems Of Identification," Automazione e Strumentazione, Dec. 2002, vol. 50, No. 11, pp. 63-69, Editrice BIAS, Italy.

Chiorescu et al., Abstract entitled "The Fingerprint Approach: Using Data Generated By A 3D Log Scanner On Debarked Logs To Accomplish Traceability In The Sawmill's Log Yard," Forest Products Journal, Dec. 2004, vol. 54, No. 12, pp. 269-276.

Chiorescu et al., Abstract entitled "The Fingerprint Method: Using Over-Bark And Under-Bark Log Measurement Data Generated By Three-Dimensional Log Scanners In Combination With Radiofrequency Identification Tags To Achieve Traceability In The Log Yard At The Sawmill," Scandinavian Journal of Forest Research, 2004, vol. 19, No. 4, pp. 274-383.

Collins, "RFID Remedy For Medical Errors," RFID Journal, 3 pages, © 2005 RFID Journal Inc.

Crossan, Abstract entitled "Recognition Technologies And The Systems Integrator," Inform, Apr. 1989, vol. 3, No. 4, pp. 26-28, USA.

Deisingh, Abstract entitled "Counterfeit Drugs," Chemistry and Industry (London), Mar. 15, 2004, No. 6, pp. 16-18.

Franzon et al., Abstract entitled "Proceedings Of SPIE—Design, Characterization And Packaging For MEMS And Microelectronics II," Proceedings of SPIE—The International Society for Optical Engineering, 2001, vol. 4593.

Grossman, Abstract entitled "Missing Movement," Scientific American, Apr. 2004, vol. 290, No. 4, pp. 26-27.

Hascher, Abstract entitled "Identifikation—vom Mikroship zur DNA," Jul. 23, 2002, vol. 51, No. 15, pp. 38-43, WEKA-Fachzeitschriften, Germany.

Hebert, Abstract entitled "Imagine The World Of SCADA Without Wires," Control (Chicago, IL) Apr. 2004, vol. 17, No. 4.

Hosaka, Abstract entitled "Feasibility Study Of Convenient Automatic Identification System Of Medical Articles Using LF-Band RFID In Hospital," Systems and Computers In Japan, Sep. 2004, vol. 35, No. 10, pp. 74-82, Scripta Technica, USA.

Li, Cheng-Ju, et al., Abstract entitled "Mobile Healthcare Service System Using RFID," 2004 IEEE International Conference on Networking, Sensing and Control, (IEEE Cat. No. 04EX761) vol. 2, pp. 1014-1019, Mar. 21-23, 2004, IEEE, Taipei, Taiwan.

Li et al., Abstract entitled "Mobile Healthcare Service System Using RFID," Conference Proceeding—2004 IEEE International Conference on Networking, Sensing and Control, Mar. 21-23, 2004.

Santra et al, Abstract entitled "Retention Of Helical Structure Of PBR-322 Covalently Closed Circular Duplex DNA At High Alkaline PH", International Journal of Biological Macromolecules, 1984, 6 (3): pp. 152-154.

Sveko et al., Abstract entitled "Microcontroller Contactless Identification System And Access Control," Informacije MIDEM, Sep. 2001, vol. 31, No. 3, pp. 185-190, Soc. Microelectron. Electron. Components & Mater.-MIDEM, Slovenia.

Svecko et al., Abstract entitled "Microcontroller Contactless Identification System And Access Control," Informacije MIDEM—Journal of Microelectronics Electronic Components and Materials, Sep. 2001, vol. 31, N. 32, pp. 185-190, SOC Microelectronics, Electron Components Materials-MIDEM, Slovenia.

Talbot, Abstract entitled "Where's The Beef From?", Technology Review, Jun. 2004, vol. 107, No. 5, pp. 48-56.

Want et al., Abstract entitled "Ubiquitous Electronic Tagging," IEEE Distributed Systems Online, 2000, vol. 1, No. 2, p. 13.

Valenstein et al., Abstract entitled "Identification Errors In Pathology And Laboratory Medicine," Clinics in Laboratories Medicine, 2004, 24/4 (979-996) U.S.

Abstract entitled "Smart Labels Tag Patients [Identification Technology]," Engineering Technology, Feb. 2005, vol. 8, No. 1, p. 22, IIE, UK.

Abstract entitled "Appleton Introduces New RFID Label Stock," Pulp and Paper Report, Aug. 2004, vol. 6, No. 15.

Abstract entitled "Focus On VLSI Market," Semicond FPD World, 2005, vol. 24, No. 3, pp. 122-123, Fig. 2, Japan.

Abstract entitled "Advanced Hardware Technologies For Ubiquitous Services," NTT Tech Rev, 2004, vol. 2, No. 2, pp. 48-52, Fig. 5, Ref. 9. Japan.

Hosaka, Abstract entitled "Possibility Estimation Of Realization For Convenient Automatic Identification System Of Medical Articles Using LF Band RFID In Hospital," Transactions of the Institute of Electronics, Information and Communication Engineers, 2003, vol. J86-D-2, No. 4, pp. 571-578, Japan.

Abstract entitled "Research Report On Patent Application Trend In Electronic Lock System Technology," 2002, pp. 238P, Fig. 76, Tbl. 132, Ref. 25., Japan.

Abstract entitled, "FDA Talk Paper," FOI Services Full Text, Mar. 28, 2005.

Abstract entitled, "Device Patients Among Targets Of RFID Chip," Devices & Diagnostics Letter, Oct. 18, 2004, vol. 321, No. 41.

Abstract entitled, "Implantable RFID Chips Moved Into Class II," Devices & Diagnostics Letter, Dec. 17, 2004, vol. 31, No. 50.

Abstract entitled, "FDA Clears Verichip For Medical Applications In The U.S.," FDA News Device Daily Bulletin, Oct. 14, 2004, vol. 1, No. 197.

Communications of the ACM, RFID, "The Importance Of Affective Quality," Sep. 2005, vol. 48, No. 9, pp. 1, 3, 31-79, ACM.

Stajano, "RFID Is X-Ray Vision," Communications of the ACM, RFID, Sep. 2005, vol. 48, No. 9, pp. 31-33.

Borriello, "RFID: Tagging The World," Communications of the ACM, RFID, Sep. 2005, vol. 48, No. 9, pp. 34-38.

Smith, et al., "RFID-Based Techniques For Human-Activity Detection," Communications of the ACM, RFID, Sep. 2005, vol. 48, No. 9, pp. 39-45.

Raskar et al., "Photosensing Wireless Tags For Geometric Procedures," Communications of the ACM, RFID, Sep. 2005, vol. 48, No. 9, pp. 46-52.

Pering, "Spontaneous Marriages Of Mobile Devices And Interactive Spaces," Communications of the ACM, RFID, Sep. 2005, vol. 48, No. 9, pp. 53-59.

His et al., "RFID Enhances Visitors' Museum Experience At The Exploratorium," Communications of the ACM, RFID, Sep. 2005, vol. 48, No. 9, pp. 60-65.

Ohkubo et al., "RFID Privacy Issues And Technical Challenges," Communications of the ACM, RFID, Sep. 2005, vol. 48, No. 9, pp. 66-72.

Günther, "RFID And The Perception Of Control: The Consumer's View," Communications of the ACM, RFID, Sep. 2005, vol. 48, No. 9, pp. 73-76.

Eckfeldt, "What Does RFID Do For The Consumer?," Communications of the ACM, RFID, Sep. 2005, vol. 48, No. 9, pp. 77-79.

\* cited by examiner

SYSTEM PROVIDING MEDICAL PERSONNEL WITH IMMEDIATE CRITICAL DATA FOR EMERGENCY TREATMENTS

CROSS-REFERENCE TO RELATED APPLICATIONS

This patent application claims the benefit of U.S. Provisional Patent Application No. 60/711,318, filed Aug. 25, 2005.

FIELD OF THE INVENTION

The present invention relates generally to emergency response systems, and more particularly to emergency information retrieval and display.

BACKGROUND OF THE INVENTION

During emergency situations, medical, rescue, and security industry workers frequently encounter persons that are unconscious or otherwise unable to communicate. Yet, such persons often require immediate medical attention. Often, such situations arise outside of the controlled environment of a hospital setting and additional time is required to transport the victim to the nearby medical facility. Upon arrival to the nearby hospital, however, the medical personnel need yet additional time to obtain the victim's critical information prior to providing the required medical care. In case of urgent blood transfusions, for example, it is of utmost importance to obtain the victim's blood type prior to commencing the required procedure. Thus, the time lost during transport to the hospital, as well as during running the necessary tests to obtain the victim's medical information, is likely to greatly decrease the risk of survival for some victims. Therefore, having immediate access to victim's critical information is imperative to patient survival.

While medical identification cards and bracelets with imprinted medical and emergency contact information may provide the required information to the on-site emergency personnel, the emergency personnel still need to allocate time to verify that the imprinted information actually belongs to the person in possession of the card or bracelet in order to prevent potentially deadly mistakes during treatment. This may require the emergency personnel to spend time to locate the victim's wallet in order to cross-reference the information on the card or bracelet with that on a driver's license or photo id, for example. If other identification is lost during the emergency, such verification may not be possible, which increases the risk to the patient. In addition to needing time to verify the identity of the victim or patient, the emergency personnel need to allocate time to convey whatever information they do find to the nearby medical facilities. This results in yet further delays prior to commencing patient treatment and increases the risk to the patient.

Furthermore, in above situations, the emergency personnel are not always able to promptly notify the third parties associated with the victim. This further decreases the flow of necessary information and eliminates the chances of promptly obtaining the critical information about the victim from the third parties prior to treatment. Disaster recovery strategies require real time acquisition of personal data with verification and location.

BRIEF SUMMARY OF THE INVENTION

The invention provides urgent/emergency service personnel with critical data about a person or animal, within the first few minutes of an encounter for treatment or identification and allows verification that the critical data describes the person or animal being treated or identified. Although the following description refers to "persons," the invention is equally applicable to animals or any living thing that may be in a position of needing immediate medical care in a situation in which critical medical history is required for successful treatment.

In one embodiment, a person having a wireless transponder, such as a Radio Frequency Identification (RFID) transponder, on his person provides the health care or security personnel with the critical information even when unconscious or dead, when the health service provider or security personnel employs a device or terminal that reads the RFID transponder. The terminal or reader interacts with a health or security service provider via an RFID signaling tag. The terminal includes a point and click user application to avail itself of data presented by an RFID tag as well as data presented from another database to which the tag might refer. The terminal activates a software application that is contained either in the RFID tag, the terminal, or in the database. The software application includes functionality that allows it to query and download certain information or programs that allow immediate and coordinated information transfer to a network. The network could be a health care system, emergency response team, military, industrial or biologic system, for example. In one embodiment, the network includes livestock and domestic animal applications. The RFID tag is the healthcare record. It relates and integrates into a larger database and network. It proves its owner and through wireless technology identifies location and other data characteristics of its owner.

The transponder attaches to a person or animal in any of a number of ways, including a wristband, necklace, ankle bracelet, wristwatch, pin, ID card or a subcutaneous capsule, for example. In one embodiment, the transponder is encased in a flexible silicone wristband that is impervious to weather and water. The transponder, after being interrogated by the reader, supplies the health or security service provider with HIPPA protected critical data such as name, blood type, allergies, directives, medicines, and emergency contact numbers. In one embodiment, the transponder also includes verification data, such as biometric verification data, for example in a form of a digital photograph of the person or animal whose critical data is on the transponder. In other embodiments, the transponder contains additional important biological data. The amount of data is only limited by the amount of memory available in the RFID tag or transponder. The reader immediately displays such critical information for the health care or security personnel on its screen.

Further, when the reader terminal is part of a wired or wireless communication device attached to a server containing a more complex and integrated database with further information about the person, the critical information about a person is presented to a health or security service provider in an immediate manner through an integrated network.

The data network consists of servers, sets of servers, and integrated software applications that allow data to be identified as belonging to the person or animal that presents its tag/RFID transponder. Therefore, the RFID tag can substantiate that it belongs to its owner. This identification process can involve biometric analysis including, but not limited to, picture (photo), retinal/iris scan, fingerprint, and palm vein scanner. Further identifiers may include DNA/RNA or dental records that are utilized as non-urgent bio identifiers. Once an RFID tag is read by the terminal, the terminal downloads additional data from a server and the additional data is presented on a reader terminal's screen. Once sent to the server network, the RFID tag signal starts a series of data retrieval and transmission algorithms. Ultimately, data transmission to a fax number, phone number, internet, text or voice file, hospital, or company, occurs in order to transmit the critical data such as blood type, allergies, or meds for critical injury to a hospital E.R, doctor, or other personnel.

In embodiments, the server queries the wireless carrier for reader terminal's location data, correlates the reader location data with hospital location data, and sends the critical information to the nearby hospitals. Additionally, the server sends alert information to other firms or individuals contained in the wristband wearer's data record.

In another embodiment, the person or animal can have a terminal reader write to an RFID transponder. This transponder can then be coupled to the person or animal. This allows emergency retrieval of pertinent healthcare identification information. A picture, voice record, ID number, can quickly be written on an RFID tag and placed on an animal. After writing to the tag, the information is time, date, and GPS stamped and sent to a network.

DETAILED DESCRIPTION OF THE INVENTION

A critical data retrieval and display system provides the urgent/emergency service personnel with critical data about a person or animal, within the first few minutes of an encounter for treatment or identification and allows verification that the critical data describes the person or animal being treated or identified. In one embodiment, a person or animal having a wireless transponder, such as a Radio Frequency Identification (RFID) transponder, on his person provides the health care or security personnel with the critical information even when unconscious or dead, as long as the health service provider or security personnel employs a device or terminal that is capable of reading the RFID transponder. The terminal or reader interacts with a health or security service provider via an RFID signaling tag. The terminal includes a point and click user application to avail itself of data presented by an RFID tag as well as data presented from another database to which the tag might refer. In one embodiment, the terminal is a stand-alone terminal, while in other embodiments the terminal is part of another device, such as a cellular phone, for example. In one embodiment, the terminal includes circuitry for determining its approximate location—e.g., a global position system or GPS. Location information can be communicated automatically to a remote site for use by emergency personnel to dispatch additional assistance. Date, time, and GPS data can be stamped on any terminal RFID tag.

The terminal activates a software application that is contained either in the RFID tag, the terminal, or in a remote database. The software application includes functionality that allows it to query and download certain information or programs that allow immediate and coordinated information transfer to a network. The network could be a health care system, emergency response team, military, industrial or biologic system, for example. In one embodiment, the network includes livestock and domestic animal applications.

The transponder attaches to a person or animal in any of a number of ways, including a wristband, necklace, ankle bracelet, wristwatch, pin, ID card or a subcutaneous capsule, for example. The transponder, after being interrogated by the reader, supplies the health or security service provider with protected critical data such as name, blood type, allergies, directives, medicines, and emergency contact numbers. HIPPA protection can be incorporated in any system via encryption technology and keys. In one embodiment, the transponder also includes verification data, such as biometric verification data, for example in a form of a digital photograph of the person or animal whose critical data is on the transponder. In other embodiments, the transponder contains additional important biological data. The amount of data is only limited by the amount of memory available in the RFID tag or transponder. The reader immediately displays such critical information for the health care or security personnel on its screen.

Further, when the reader terminal is part of a wired, or wireless communication device attached to a server containing a more complex and integrated database with further information about the person, or when the reader is attached, either with a cable or wirelessly, to a computer containing further data about the person, all such data (if it were health data) would be HIPPA protected, and thus secure. Such data is also displayed on the reader or made otherwise available, such as through email, phone, or fax, for example. In this way, critical information about a person is presented to a health or security service provider in an immediate manner through an integrated network.

The data network consists of servers, sets of servers, and integrated software applications that allow data to be identified as belonging to the person or animal that presents its tag/RFID transponder. Therefore, the RFID tag can substantiate that it belongs to its owner. This identification process can involve biometric analysis including, but not limited to, picture (photo), retinal/iris scan, fingerprint, and palm vein scanner. Further identifiers may include DNA/RNA or dental records that are utilized as non-urgent bio identifiers. Once an RFID tag is read by the terminal, the terminal downloads additional data from a server and the additional data is presented on a reader terminal's screen. The RFID tag signal, once sent to the server network, starts a series of data retrieval and transmission algorithms, some customized by the person or company/business wearing an RFID tag. Ultimately, data transmission to a fax number, phone number, internet, text or voice file, hospital, or company, occurs in order to transmit the critical data such as blood type, allergies, or meds for critical injury to a hospital E.R, doctor, or other personnel.

The RFID tag reader terminal may also interact with other software applications in real time when initiated by tag reading. This interrogation of the tag by the terminal may include multiple signals if the tag includes multiple RFID chips. The terminal may also write to the RFID tag as part of an initiated software application. In this way, the reader terminal may write important health or bio-identification information to a newly placed RFID tag band. The newly placed band is incorporated into a data network.

This platform provides for immediate presentation of critical data. It has a particular application for health care urgency delivery for injured people or those in an emergency or disaster situation. Bio-identification is an important aspect in ensuring proper use of the critical data. Preferably, the platform utilizes the RFID tag as an energy-efficient carrier of a health/data record regarding its owner. Medical/health data, such as medications, are also mission critical and part of the data presented.

Figure 1:
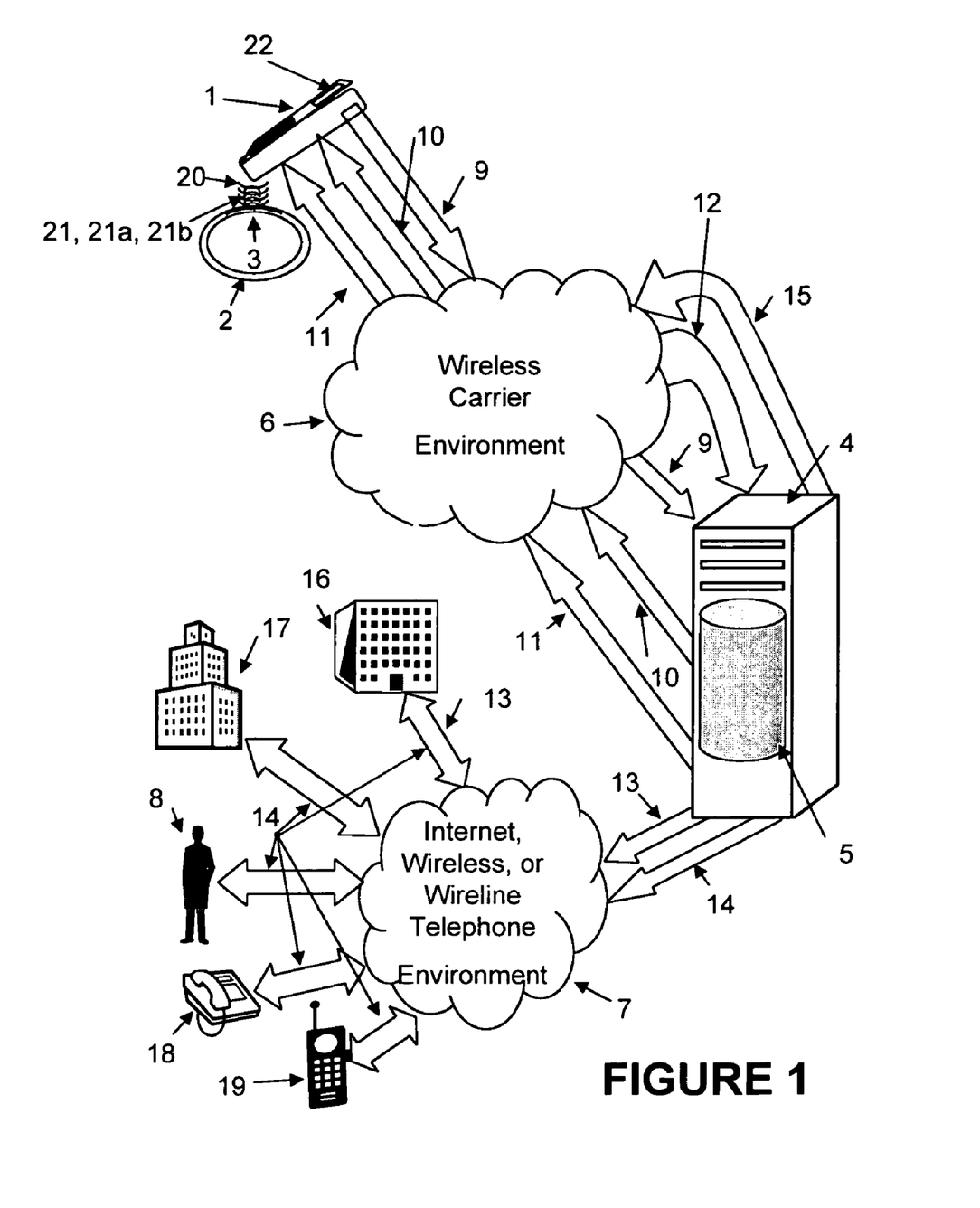
FIG. 1 is schematic diagram of the system showing the major components, including the RFID reader/transmitter/receiver/display, the wristband with the embedded RFID transponder, the wireless environment that the reader and server employ to communicate, the server with the resident database, and the wireless/internet/telephone environment used by the server to communicate with hospitals or other entities.

Referring to FIG. 1, a health care or security personnel employs a reader terminal 1 having a wireless interface. In this embodiment, the terminal 1 employs an RFID interface to communicate with a transponder 3. The terminal 1 sends an energizing signal 20 to the transponder 3 embedded in a silicone wristband 2 that is worn by a person in need of immediate medical attention. The energizing signal 20, in turn, elicits a return signal 21 from the transponder 3. The return signal 21 contains data that is read, interpreted and stored in the reader 1. The data is then available for display on the reader screen 22. Part of the data retrieved from the transponder 3 is the ID number 21a of the wristband 2. Software resident in the reader 1 causes the ID number 21a of the wristband 2 to be transmitted wirelessly 9 to a server 4. There, the ID number 21a is compared to data contained in a database 5 resident on the server 4. Once the ID number 21a matches an identical number 26a in a table 26 (FIG. 8) of the database 5, an image of the wristband owner and/or other verification information, such as additional biometric identifiers, stored in another table 27 (FIG. 8) in the database 5 is sent wirelessly 10 back to the reader 1 where it is available for display. The image can be compared to the victim to ensure that the wristband wearer is in fact the owner of the wristband 2, and is therefore the person whose critical data has been read by the reader 1. Subsequent to the image being transmitted to the reader 1, the database 5 sends additional, supporting medical data 11 to the reader 1 that is stored in the reader 1 and is then available for display on the reader's screen 22.

The software running on the server 4 next will query 15 the wireless carrier 6 for location data 12 pertaining to the reader 1. Location data 12 could be provided by GPS or conventional cell tower triangulation methods. Using the location data 12 provided by the wireless carrier 6 the server 4 would employ a hospital location table 28 in the server database 5 and compare the reader location data 12 to a resident listing of hospital locations and would proceed to transmit 7 either wirelessly, through the internet or via telephone, for example, the critical medical data 13 of the wristband wearer to hospitals 16 near to the location of the wristband wearer and the assisting health care worker. The critical medical data 13 would therefore be available immediately to the hospital staff should the wristband wearer be transported to their hospital.

Additionally, the server could send alert information 14 to other firms 17 or individuals 8 contained in the wristband wearer's data record. These firms or individuals could be other family members, other physicians, or the wristband wearer's employer. Information can also be transmitted to via robotic voice to a radio 19 or telephone 18. In all cases, alert information 14 could be procured from the server by those with proper clearance.

Figure 2:
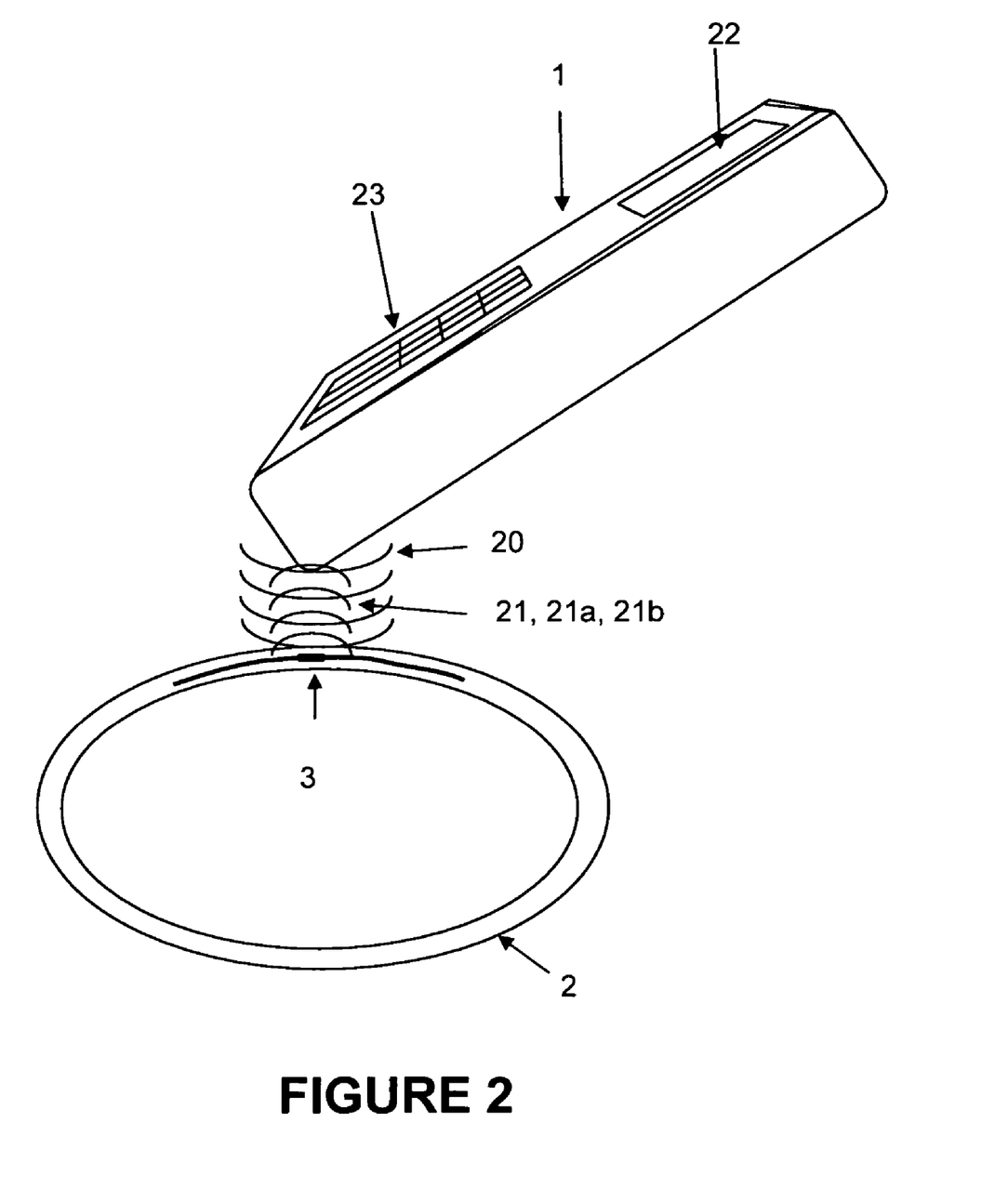
FIG. 2 is a perspective view of the reader and the wristband showing a signal from the reader that allows the transponder to generate a return signal to the reader, which provides critical information about the wearer of the wristband.

Referring to FIG. 2, the RFID reader 1 sends a signal 20 to the transponder 3 in the wristband 2, thereby exciting the antenna in the transponder 3 and causing the transponder 3 to transmit a signal 21 back to the reader 1. The signal 21 contains the wristband owner's ID number 21a and critical medical information 21b. The reader 1 receives and stores the ID number 21a and the medical data 21b. In addition to waking up the transponder 3, the signal 20 may also write to the transponder identification information for use in managing and tracking the wearer through a process, which can be either standardized or ad hoc (e.g., an emergency treatment process developed to handle critical care tailored to the situation). By adding the identification information, the wearer can be accurately tracked.

Initially, because current models of transponders have limited memory capacity to store this critical data, it will be necessary to highly encode the data to consume as little memory space as possible. As technology improves, eventually all of the critical and personal data about the wristband owner could be stored in the transponder 3. In one embodiment, the critical data stored on the transponder 3 contains the owner identifier 21a, critical medical data 21b, emergency contact data, and directives (such as DNR, organ donation, or power of attorney) In an embodiment, the transponder 3 also includes verification data, such as biometric identifiers of the wristband's owner (a digital photograph, fingerprint, dental, RNA/DNA records). The critical medical data 21b comprises blood type, medicines, allergies and the like. Software in the reader 1 interprets the received information and displays the information on the reader's screen 22. In an embodiment, when transponder 3 does not include verification data, the reader 1 transmits the ID number 21a wirelessly to a server 4 (FIGS. 1, 8) where it is matched to the owner's picture, or other biometric data. Once the match is made, the server 4 wirelessly transmits the picture or other biometric data to the reader 1 where it is displayed on the reader's screen 22. The reader user can then use the picture displayed to confirm the wristband wearer is the wristband owner. The server 4 also wirelessly sends additional medical data 11 (FIG. 1) to the reader 1 where it is stored for later display on the reader screen 22, such as when called up by using the keypad 23 on the reader 1.

Figure 3:
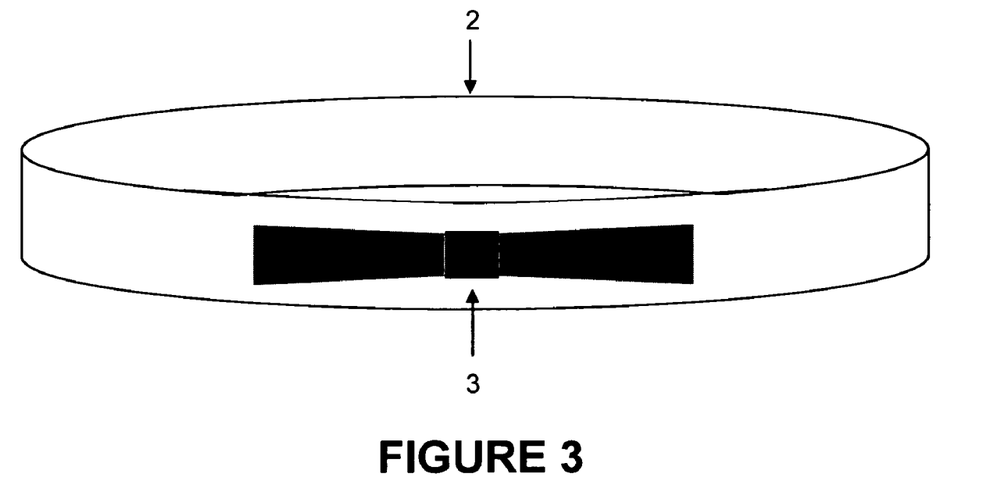
FIG. 3 is a perspective view of the wristband of FIG. 2 showing the internal placement of the RFID transponder inside the wristband.
Figure 4:
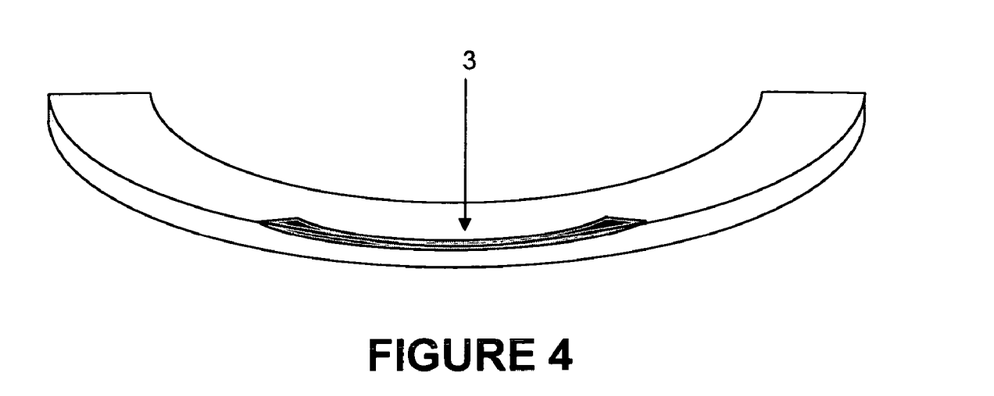
FIG. 4 is perspective partial lateral view of the wristband of FIG. 2 showing the internal placement of the RFID transponder inside the wristband.
Figure 5:
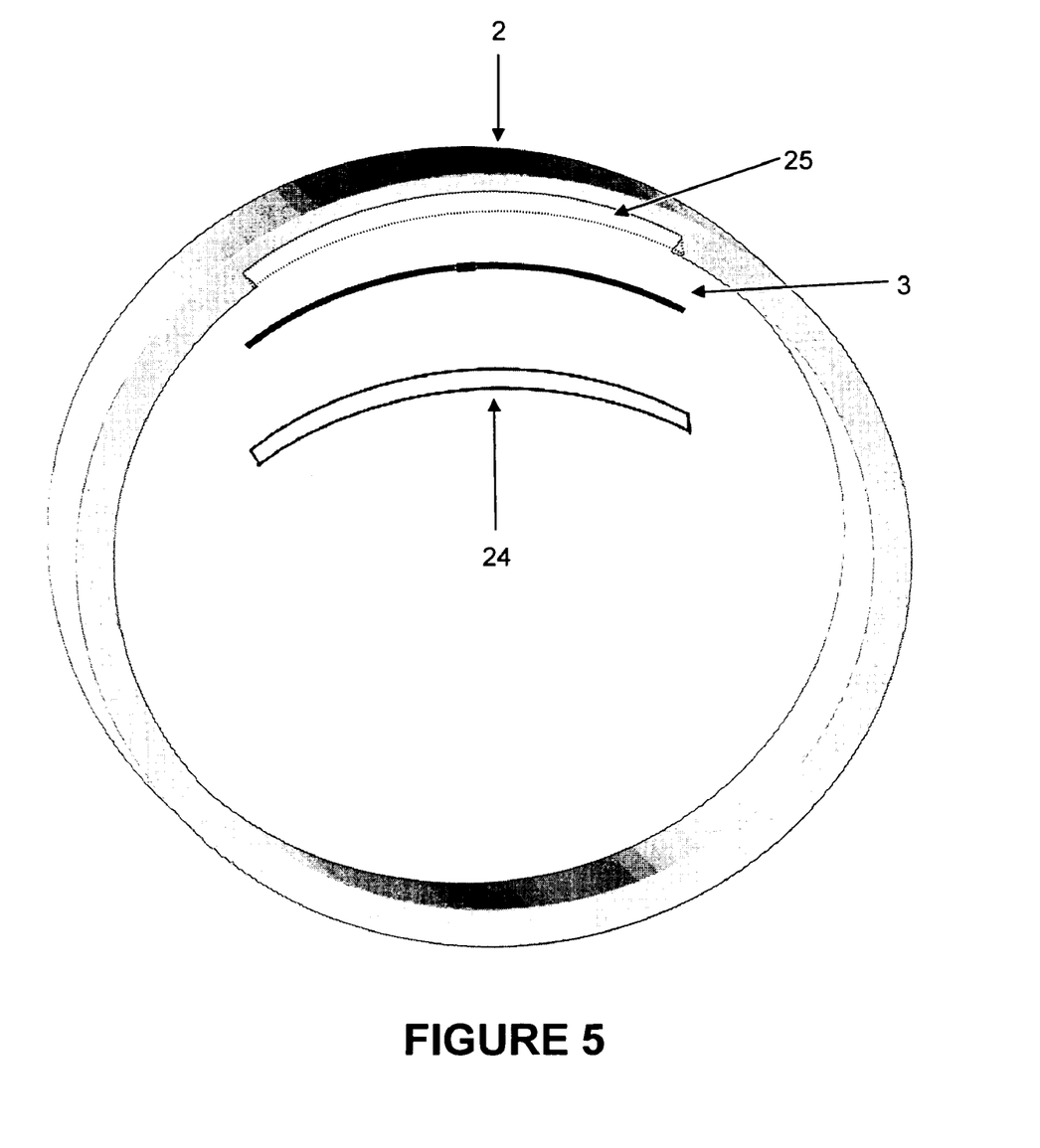
FIG. 5 is another perspective view of the wristband of FIG. 2 indicating the placement of the transponder inside the wristband and depicting a cavity that is molded into the wristband during manufacture, as well as a plug that covers the transponder after it is inserted in the wristband. In the illustrated embodiment, the plug is held in place with silicone cement.
Figure 6:
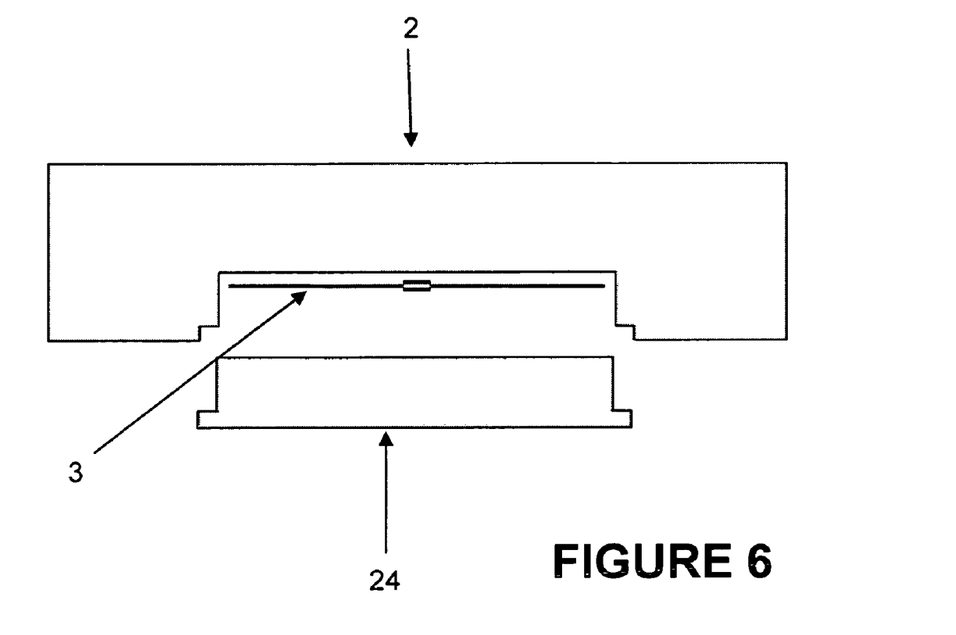
FIG. 6 is a cross-sectional view of the wristband of FIG. 2 showing the cavity molded into the wristband during manufacture, the RFID transponder inserted into the cavity, and the relationship of the plug to the wristband cavity.
Figure 7:
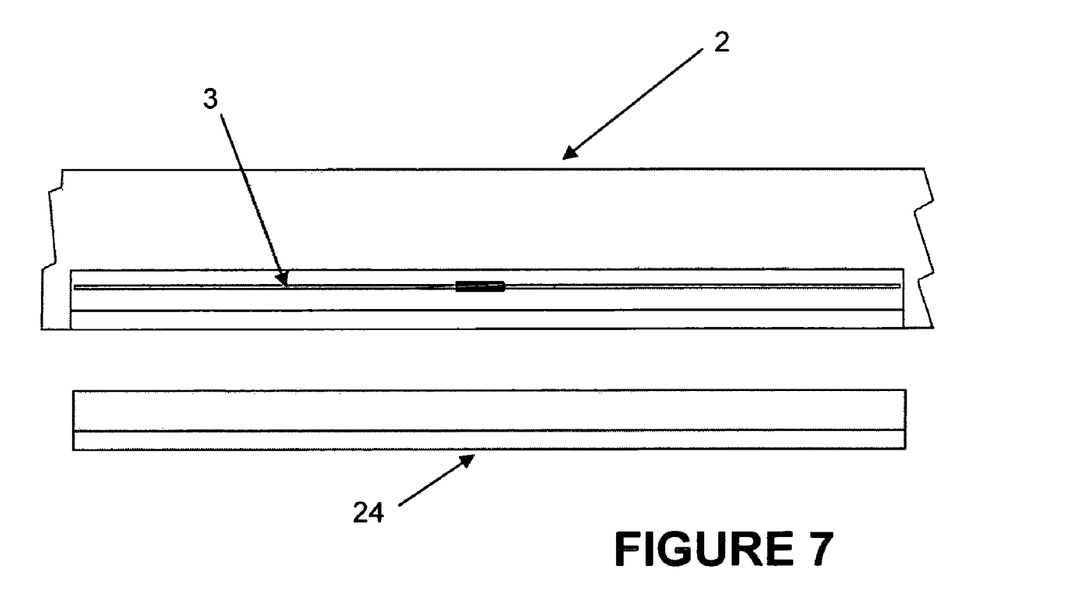
FIG. 7 is an additional cross-sectional view of the wristband of FIG. 6.

As seen in FIGS. 3 and 4, the RFID transponder 3 is encased in a flexible silicone wristband 2 that is impervious to weather and water. As shown in FIGS. 5-7, because the RFID transponder 3 may not be able to withstand the high heat generated by molten silicone, the wristband 2 is molded with a cavity 25 that is of a size adequate to allow the insertion of the transponder 3. A plug 24, also manufactured of silicone, is of the exact shape and size as to be able to completely fill the cavity 25 and will be held securely in place with silicone cement. The plug 24 is put in place and sealed during the manufacturing process.

Figure 8:
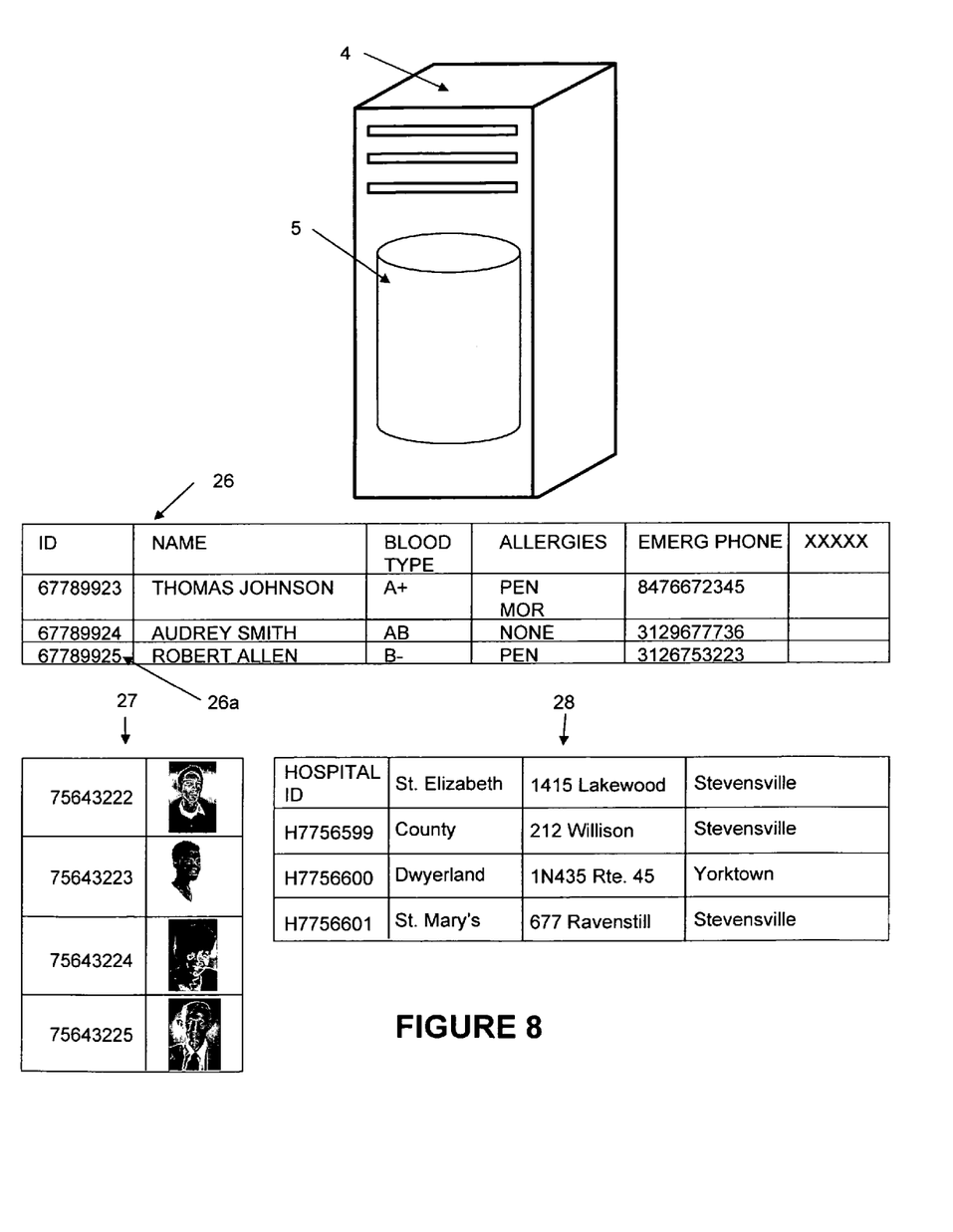
FIG. 8 is a perspective view of the server in which the identification, medical, reader location, and hospital location databases reside, and also showing exemplary embodiments of each of the databases.

Referring to FIG. 8, the server 4 contains the tables that are used by the system database 5. The wristband owner table 26 contains all of the wristband owner's medical and other personal data. The identification table 27 contains verification data, such as visual and other biometric data of the wristband owner, which is used to prove wristband ownership. The hospital location table 28 is used to locate hospitals within range of the wristband wearer in times of emergency. In an embodiment, this portion of the database 5 also contains a list of sites, such as hospitals or service facilities, which provide initial setup and information transfer or updates for the transponder 3.

Figure 9:
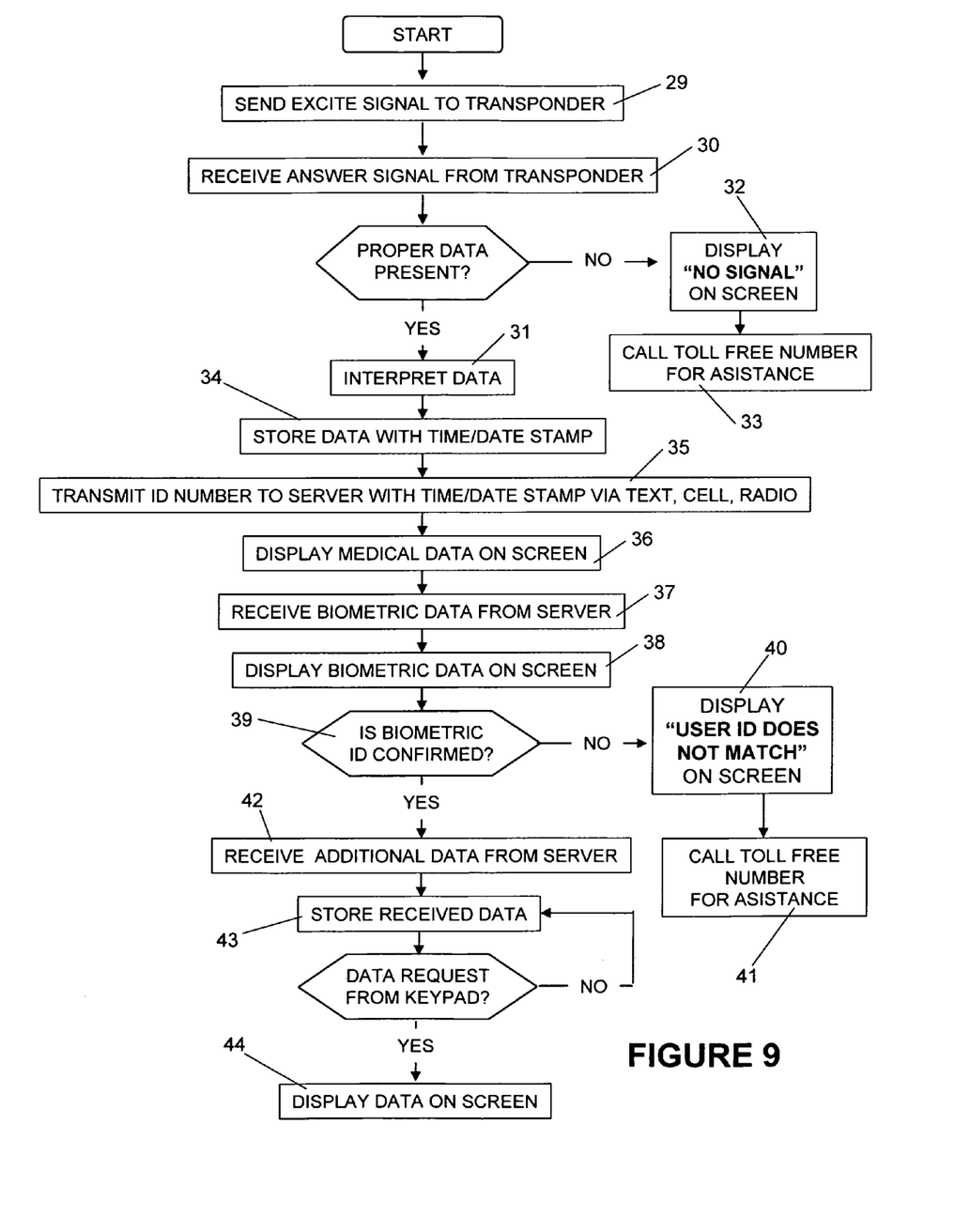
FIG. 9 is a flow diagram depicting an embodiment of a process executed by the software resident in the terminal/reader.

Referring to FIG. 9, in one embodiment, the software in the reader 1 need not be running at all times. Pressing a key on the reader keyboard 23 (FIG. 2) will start the software and prepare it to receive data from the RFID reader's wireless interface. Another key on the keyboard will start the RFID transponder reading process by sending 29 the signal 20 (FIG. 2) to the transponder 3. This signal causes a return signal 21 (FIG. 2) to be sent from the transponder, wherein the signal 21 carries the data stored in the transponder memory, and received 30 by the reader. If the data received is proper, the software running on the reader receives the data and interprets it (step 31). If the data is absent or is formatted improperly, the screen on the reader will display the words "NO SIGNAL" 32 and the reader will immediately place a wireless call 33 to a help center. Pressing another key would cause the terminal to write to the RFID tag.

The data interpreted by the reader software will be stored 34 along with the date and time stamp in the reader memory. Part of the data received from the transponder is the wristband owner's ID number 21*a* (FIG. 2). This number is transmitted 35 wirelessly to a server 4 where database 5 containing information regarding the wristband owner is stored. At the same time, the critical medical data that was received from the transponder is displayed 36 on the reader screen.

The ID number 21*a* (FIG. 2) sent by the reader is compared to a list of ID numbers 26*a* (FIG. 8) in the database 5. If there is a match, the picture and/or other biometric data showing proof of wristband ownership is transmitted wirelessly back to the reader, along with additional medical and personal data. After the reader receives 37 the biometric data from the server, the wristband owner's picture, and/or other biometric verification data, is displayed 38 on the reader screen. The reader then queries the user to match the picture with the wristband wearer, asking if there is a match 39. If the picture does not match the wearer, the user will indicate so by using the keypad. At that point, the reader screen displays "USER ID DOES NOT MATCH" 40 and the reader will immediately place a wireless call 41 to a help center. If the reader user indicates with the keyboard that a match exists, the reader then receives 42 and stores 43 the additional medical and personal data from the server. The reader displays 44 the received additional data on the display screen when the reader user inputs a request via the keypad.

The use of the term "animal" in the following claims is intended to include both humans and lower forms of life. The use of the term "treatment center" in the following claims is intended to include by way of example, hospitals, field hospitals, morgues, or any command and control post set up for handling critical information. Also, the use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A critical data retrieval and display system for providing a medical record comprising a first and a second sets of data, the system comprising:
   a device attached to an animal and containing the first set of data describing information required for an urgent treatment, wherein the first set of data is held by the device in a manner to maintain them confidential, the first set of data including information identifying the animal;
   means for assuring the first set of data in the device belongs to the animal;
   a reader for communicating with the device, displaying at least the first set of data of the medical record and transmitting at least the information identifying the animal; and
   a remote server receiving the transmission from the reader, identifying the second set of data from the information identifying the animal and providing the second set of data to the reader.

2. The system of claim 1 wherein the device includes a tamper proof mechanical coupling for securely affixing the device to the animal.

3. The system of claim 1 wherein at least one of the first and second sets of data includes one or more of (1) biometric data describing one or more biological conditions of the animal and (2) biometric data from a trusted source.

4. The system of claim 1 wherein the first set of data further comprises at least one of medical data, emergency contact data, and directives data.

5. The system of claim 3 wherein the biometric data comprises at least one of an object photograph, a fingerprint, a dental record a DNA record, an iris scan and an RNA record.

6. The system of claim 1 wherein the remote server includes at least an electronic database and the electronic database stores at least a device owner table, an identification table, and a medical triage location table.

7. The system of claim 1 wherein the server identifies one or more treatment centers near the animal, alerts one or more of the treatment centers, and sends the second set of data to the one or more treatment centers.

8. The system of claim 1 wherein the reader communicates with the device via an RFID interface to both read and write information to and from the device.

9. The system of claim 1 wherein the server sends alert information to predetermined entities in response to receiving the information identifying the animal from the reader.

10. The system of claim 1 where the reader is configured to update the first set of data at the device during the urgent treatment.

11. The system of claim 1 wherein the reader includes a first transponder for providing a first communication session between the reader and the device.

12. The system of claim 11 wherein the reader includes a second transponder for providing a second communication session between the reader and the remote server.

13. The system of claim 10 wherein at least one of the first and second sets of data includes one or more of a picture a voice record, a time a date, and location information.

14. A device associated with an animal for use in urgent treatment, the device comprising:
a tamper resistant housing worn by the animal;
a memory for storing a first set of data, the first set of data including information identifying the animal; and
a transponder for wirelessly communicating at least the information identifying the animal to a reader in response to an excitation signal, wherein the reader is configured to wirelessly transmit the information identifying the animal to a remote server for authenticating the animal and to receive a second set of data from the remote server, the second set of data transmitted by the remote server in response to receiving the information identifying the animal, the first set of data and the second set of data comprising a patient medical record.

15. The device of claim 14 including a tamper proof mechanical coupling for securely affixing the device to the animal.

16. The device of claim 14 wherein the remote server authenticates the animal by comparing the information identifying the animal with information from a trusted source.

17. The device of claim 14 wherein the transponder includes an RFID interface for providing wireless communication between the device and the reader.

18. The device of claim 14 wherein at least one of the first and second sets of data comprises at least one of object medical data, emergency contact data, and directives data.

19. The device of claim 14 wherein the transponder receives an update to the first set of data for storing in the memory during the urgent treatment.

20. The device of claim 19 where the update to the first set of data includes information identifying the animal.

21. The device of claim 19 wherein the transponder further includes an interface for communicating with a computer network.

22. The device of claim 19 wherein the update to the first set of data includes one or more of a picture, a voice record an ID number a time, a date, and location information.

23. A method for retrieving and displaying data associated with an animal for use in urgent treatment, the method comprising:
transmitting an excitation signal in a first communication session between a device worn by the animal and a reader operated by a first responder personnel;
retrieving a first set of data during the first communication session from the device worn by the animal, wherein the first set of data includes at least information uniquely identifying the animal;
transmitting the identification information in a second communication session to a remote server;
comparing the information received at the remote server with information maintained at the remote server in order to identify a second set of data that when matched with the first set of data provides a complete medical record of the animal; and
returning to the reader operated by the first responder personnel at least some information in the second set of data for use in the urgent treatment of the animal.

24. The method of claim 23 wherein at least one of the first and second sets of data comprises at least one of medical data, emergency contact data, and directives data.

25. The method of claim 23 wherein comparing the information received at the remote server with information maintained at the remote server includes correlating an object identifier number to biometric verification data and displaying the biometric verification data.

26. The method of claim 23 wherein at least one of the first and second sets of data includes biometric verification data including at least one of an object photograph, a fingerprint a dental record, a DNA record an iris scan, and an RNA record.

27. The method of claim 23 further comprising:
looking up the identification number in an owner table stored on the server;
identifying the second set of data according to the identification number; and
transmitting the second set of data to the reader for displaying at the reader.

28. The method of claim 23 including communicating during the second communication session a location of the animal to the remote server in order for the remote server to locate one or more accessible medical resources based on the location and communicate to the first responder personnel locations of the one or more resources; and
communicating from the remote server to the one or more resources the complete medical record of the animal.

29. The method of claim 23 including verifying the device has not been tampered with.

30. The method of claim 23 including transmitting a set of updated biometric data to the device during the urgent treatment.

31. The method of claim 30 wherein the set of updated biometric data includes information identifying the animal.

32. The method of claim 30 including sending the set of updated biometric data to the server for storage.

33. The method of claim 30 wherein the set of updated biometric data includes one or more of a picture a voice record an ID number a time a date, and location information.

34. The system of claim 1, wherein the reader includes means for determining a location of the animal for transmission to the remote server, and the remote server includes instructions responsive to the location for identifying one or more resources accessible from the location that provide medical services.

35. The system of claim 34 wherein the remote server includes instructions for transmitting the medical record to the one or more resources.

36. The system of claim 13, wherein the reader includes a mobile phone device having a capability of reproducing the voice record.

37. The system of claim 1 wherein the device attached to the animal is implanted under the animal's skin.

38. The system of claim 1 wherein the device includes memory for maintaining the first set of data, which memory can be both read from and written to by the reader.

39. The device of claim 14 wherein the memory is a read/write memory that allows the reader to both read from and write to the first set of data.

40. The device of claim 14 is implanted under the animal's skin.

41. The method of claim 23 wherein the device worn by the animal is implanted under the animal's skin.

42. The method of claim 23 including writing to a memory maintaining the first set of data.

* * * * *